US006440735B1

(12) United States Patent
Gaeta

(10) Patent No.: US 6,440,735 B1
(45) Date of Patent: Aug. 27, 2002

(54) DENDRITIC CELL VACCINE CONTAINING TELOMERASE REVERSE TRANSCRIPTASE FOR THE TREAMENT OF CANCER

(75) Inventor: Federico C. A. Gaeta, Mountain View, CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 09/675,321

(22) Filed: Sep. 28, 2000

Related U.S. Application Data

(63) Continuation of application No. PCT/US99/06898, filed on Mar. 30, 1999.
(60) Provisional application No. 60/112,006, filed on Mar. 31, 1998.

(51) Int. Cl.[7] .......................... C12N 5/08; A01N 63/00; A61K 48/00
(52) U.S. Cl. ................ 435/372.2; 435/372.3; 424/93.21
(58) Field of Search .......................... 435/372.2, 372.3; 424/93.21

(56) References Cited

U.S. PATENT DOCUMENTS

| | | | |
|---|---|---|---|
| 4,839,290 A | 6/1989 | Kaieda et al. ......... 435/240.23 |
| 5,583,016 A | 12/1996 | Villeponteau et al. ..... 435/91.3 |
| 5,645,986 A | * 7/1997 | West et al. ..................... 435/6 |
| 5,648,219 A | 7/1997 | MacKay et al. ................ 435/6 |
| 5,656,638 A | * 8/1997 | Gaeta et al. ................ 514/301 |
| 5,747,317 A | 5/1998 | Cao .......................... 435/194 |
| 5,770,422 A | 6/1998 | Collins ....................... 435/194 |
| 5,858,777 A | 1/1999 | Villeponteau et al. ...... 435/325 |
| 5,866,115 A | 2/1999 | Kanz et al. ................ 424/93.7 |
| 5,871,728 A | 2/1999 | Thomson et al. .......... 424/93.7 |
| 5,874,307 A | 2/1999 | Ohno et al. ............. 435/372.3 |
| 5,917,025 A | 6/1999 | Collins ...................... 536/23.2 |
| 5,962,318 A | 10/1999 | Rooney et al. ............. 435/325 |
| 5,962,320 A | * 10/1999 | Robinson .................... 435/366 |
| 5,968,506 A | * 10/1999 | Weinrich et al. ........... 424/94.5 |
| 5,972,627 A | 10/1999 | Galy ......................... 435/7.21 |
| 5,981,707 A | 11/1999 | Harrington et al. ......... 530/350 |
| 5,994,126 A | 11/1999 | Steinman et al. ........... 435/325 |
| 6,004,807 A | 12/1999 | Banchereau et al. ........ 435/325 |
| 6,008,004 A | 12/1999 | Olweus et al. ............. 435/7.24 |
| 6,010,905 A | 1/2000 | Cohen et al. ............... 435/372 |
| 6,015,554 A | 1/2000 | Galy ......................... 424/93.7 |
| 6,017,527 A | 1/2000 | Maraskovsky et al. .. 424/93.71 |
| 6,033,669 A | 3/2000 | Jondal ..................... 424/193.1 |
| 6,077,519 A | 6/2000 | Storkus et al. ........... 424/277.1 |
| 6,080,409 A | 6/2000 | Laus et al. ............... 424/192.1 |
| 6,093,809 A | 7/2000 | Cech et al. ................. 536/23.5 |
| 6,166,178 A | * 12/2000 | Cech et al. ................. 530/324 |
| 6,224,870 B1 | * 5/2001 | Segal ....................... 424/192.1 |
| 6,261,836 B1 | * 7/2001 | Cech et al. ................. 435/325 |
| 6,277,613 B1 | 8/2001 | De Lange et al. .......... 435/193 |

FOREIGN PATENT DOCUMENTS

| | | |
|---|---|---|
| CH | 689672 A9 | 2/2000 |
| WO | WO 93/20185 | 10/1993 |
| WO | WO 94/02156 | 2/1994 |
| WO | WO 94/21287 | 9/1994 |
| WO | WO 94/28113 | 12/1994 |
| WO | WO 95/34638 | 12/1995 |
| WO | WO 96/23060 | 8/1996 |
| WO | WO 97/04802 | 2/1997 |
| WO | WO 97/07200 | 2/1997 |
| WO | WO 97/22349 | 6/1997 |
| WO | WO 97/24447 | 7/1997 |
| WO | WO 97/29182 | 8/1997 |
| WO | WO 97/29183 | 8/1997 |
| WO | WO 97/40182 | 10/1997 |

(List continued on next page.)

OTHER PUBLICATIONS

Nakamura et al., Science 277 (5328), 955–959 (Aug. 15, 1997).*
Banchereau, J., et al., "Dendritic Cells and the Control of Immunity", Nature, 392:245–252 (1998).
Banchereau, J., et al., "Immunobiology of Dendritic Cells", Annu. Rev. Immunol., 18:767–811 (2000).
Cong, YS., et al., "The Human Telomerase Catalytic Subunit hTERT: Organization of the Gene and Characterization of the Promoter", Human Molecular Genetics, 8(1):137–142 (1999).
Greaves, M., Is Telomerase Activity in Cancer Due to Selection of Stem Cells and Differentiation Arrest?, Trends Genet., 12(4):127–128 (1996).
Greenberg, R.A., et al., "Telomerase reverse transcriptase gene is a direct target of c–Myc but is not functionally equivalent in cellular transformation", Oncogene, 18:1219–1226 (1999).
Greener, M., "Telomerase: The Search for a Universal Cancer Vaccine", Molecular Med. Today, 6:257 (2000).
Hart, D., "Dendritic Cells: Unique Leukocyte Populations Which Control the Primary Immune Response", Blood, 90(9):3245–3287 (1997).
Hsu, et al., "Vaccination of Patients With B–Cell Lymphoma Using Autologous Antigen–Pulsed Dendritic Cells", Nature Med., 2:52–58 (1996).

(List continued on next page.)

*Primary Examiner*—Kenneth R. Horlick
(74) *Attorney, Agent, or Firm*—J. Michael Schiff; David J. Earp

(57) ABSTRACT

The invention provides a method of activating a T lymphocyte by contacting the T lymphocyte with a dendritic cell (DC) that presents a telomerase reverse transcriptase (TRT) peptide in the context of a MHC class I or MHC class II molecule. The DC may be pulsed with a TRT polypeptide or may comprise a recombinant polynucleotide encoding a TRT such as hTRT. The invention also provides DCs comprising a recombinant TRT polynucleotide. The methods and compositions of the invention are used in prevention and treatment of cancers and other cell proliferation diseases or conditions.

22 Claims, 2 Drawing Sheets

FOREIGN PATENT DOCUMENTS

| WO | WO 97/41210 | 11/1997 |
| --- | --- | --- |
| WO | WO 98/01538 | 1/1998 |
| WO | WO 98/07838 | 2/1998 |
| WO | WO 98/14592 | 4/1998 |
| WO | WO 98/14593 | 4/1998 |
| WO | WO 98/15615 | 4/1998 |
| WO | WO 98/21343 | 5/1998 |
| WO | WO 98/23759 | 6/1998 |
| WO | WO 98/37181 | 8/1998 |
| WO | WO 98/46083 | 10/1998 |
| WO | WO 98/55597 | 12/1998 |
| WO | WO 98/59040 | 12/1998 |
| WO | WO 98/59046 | 12/1998 |
| WO | WO 99/01560 | 1/1999 |
| WO | WO 99/25812 | 5/1999 |
| WO | WO 99/50392 | 10/1999 |
| WO | WO 99/51255 | 10/1999 |
| WO | WO 99/63050 | 12/1999 |
| WO | WO 99/63945 | 12/1999 |
| WO | WO 00/02581 | 1/2000 |
| WO | WO 00/08191 | 2/2000 |
| WO | WO 00/15264 | 3/2000 |
| WO | WO 00/25813 | 5/2000 |
| WO | WO 00/28000 | 5/2000 |
| WO | 00/61766 | * 10/2000 |

OTHER PUBLICATIONS

Koch, et al., "Antigen Processing In Populations of Mature Murine Dendritic Cells Is Caused by Subsets of Incompletely Matured Cells", J. Immunol., 155:93–100 (1995).

Lingner, J., et al., "Purification of Telomerase from Euplotes Aediculatus: Requirement of a Primer 3' Overhang", Proc. Natl. Acad. Sci. USA, 93:10712–10717 (1996).

McArthur, et al., "Induction of Protective Anti–Tumor Immunity by Gene–Modified Dendritic Cells", J. Immunother., 21:41–47 (1998).

Meyerson, M., et al., "hEST2, the Putative Human Telomerase Catalytic Subunit Gene, Is Up–Regulated in Tumor Cells and During Immortalization", Cell, 90:785–795 (1997).

Minev, B., et al., "Cytotoxic T Cell Immunity Against Telomerase Reverse Transcriptase In Humans", PNAS, 97(9):4796–4801 (2000).

Nair, et al., "Regression of Tumors In Mice Vaccinated With Professional Antigen–Presenting Cells Pulsed With Tumor Extracts", Int. J. Cancer, 70:706–715 (1997).

Norrback, K., et al., "Telomeres and Telomerase in Normal and Malignant Heamatopoietc Cells", Eur. J. Cancer, 33(5):774–780 (1997).

Romani, N., et al., "Proliferating Dendritic Cell Progenitors in Human Blood", J. Exp. Med., 180:83–93 (1994).

Tuting, et al., "Genetically Modified Bone Marrow–Derived Dendritic Cells Expressing Tumor–Associated Viral Or "Self" Antigens Induce", Eur. J. Immunol., 27:2702–2707 (1997).

Vonderheide, R., et al., "The Telomerase Catalytic Subunit Is A Widely Expressed Tumor–Associated Antigen Recognized by Cytotoxic T Lymphocytes", Immunity, 10:673–679 (1999).

Yasui, W., et al., "Expression of Telomerase Catalytic Component, Telomerase Reverse Transcriptase, in Human Gastric Carcinomas", Jpn. J. Cancer Res., 89:1099–1103 (1998).

Young, et al., "Dendritic Cells as Adjuvants For Class I Major Histocompatibility Complex–Restricted Antitumor Immunity", J. Exp. Med., 183:7–11 (1996).

Broccoli et al., Human telomeres contain two distinct Myb–related proteins, TRF1 and TRF2, Nature Gen 17:231 (1997).

Brun et al., Proteins that bind to double–stranded regions of telomeric DNA, Trends in Cell Biol 7:317 (1997).

Chong et al., A human telomeric protein, Science 270:1663 (1995).

Greener, Telomerase: the seach for a universal cancer vaccine, Mol Med Today 6:257 (2000).

Harrington et al., A mammalian telomerase–associated protein, Science 275:973 (1997).

Heiser et al., Human dendritic cells transfected with renal tumor RNA stimulate polyclnal T–cell responses against antigens expressed by primary and metastic tumors, Cancer Res 61:3388 (2001).

Kim et al., TIN2, a new regulator of telomere length in human cells, Nature Gen 23:405 (1999).

Morin G, Is telomerase a universal cancer target? J Natl Cancer Inst 87:859 (1995).

Nair et al., Induction of cytotoxic T cell response and tumor immunity against unrelated tumors using telomerase reverse transcriptase RNA transfected dendritic cells, Nature Med 6:1011 (2000).

Pennisi E, A possible new partner for telomerase, Science 282:1395 (1998).

Vonderheide et al., The telomerase catalytic subunit is a widely expressed tumor–associated antigen recognized by cytotoxic T lymphocytes, Immunity 10:673 (1999).

Vonderheide et al., Characterization of HLA–A3–restricted cytotoxic T lymphocytes reactive against the widely expressed tumor antigen telomerase, Clin Cancer Res 7:3343 (2001).

Vonderheide et al., Equivalent induction of telomerase–specific cytotoxic T lymphocytes from tumor–bearing patients and healthy individuals, Cancer Res 61:8366 (2001).

Geron Corporation, Menlo Park, CA—Press Release, Geron Announces Initiation of Duke Prostate Cancer Clinical Trial Using Telomerase Immunotherapy, Oct. 30, 2001.

* cited by examiner

Figure 1

```
MPRAPRCRAVRSLLRSHYREVLPLATFVRRLGPQGWRLVQRGDP
AAFRALVAQCLVCVPWDARPPPAAPSFRQVSCLKELVARVLQRL
CERGAKNVLAFGFALLDGARGGPPEAFTTSVRSYLPNTVTDALR
GSGAWGLLLRRVGDDVLVHLLARCALFVLVAPSCAYQVCGPPLY
QLGAATQARPPPHASGPRRRLGCERAWNHSVREAGVPLGLPAPG
ARRRGGSASRSLPLPKRPRRGAAPEPERTPVGQGSWAHPGRTRG
PSDRGFCVVSPARPAEEATSLEGALSGTRHSHPSVGRQHHAGPP
STSRPPRPWDTPCPPVYAETKHFLYSSGDKEQLRPSFLLSSLRP
SLTGARRLVETIFLGSRPWMPGTPRRLPRLPQRYWQMRPLFLEL
LGNHAQCPYGVLLKTHCPLRAAVTPAAGVCAREKPQGSVAAPEE
EDTDPRRLVQLLRQHSSPWQVYGFVRACLRRLVPPGLWGSRHNE
RRFLRNTKKFISLGKHAKLSLQELTWKMSVRDCAWLRRSPGVGC
VPAAEHRLREEILAKFLHWLMSVYVVELLRSFFYVTETTFQKNR
LFFYRKSVWSKLQSIGIRQHLKRVQLRELSEAEVRQHREARPAL
LTSRLRFIPKPDGLRPIVNMDYVVGARTFRREKRAERLTSRVKA
LFSVLNYERARRPGLLGASVLGLDDIHRAWRTFVLRVRAQDPPP
ELYFVKVDVTGAYDTIPQDRLTEVIASIIKPQNTYCVRRYAVVQ
KAAHGHVRKAFKSHVSTLTDLQPYMRQFVAHLQETSPLRDAVVI
EQSSSLNEASSGLFDVFLRFMCHHAVRIRGKSYVQCQGIPQGSI
LSTLLCSLCYGDMENKLFAGIRRDGLLLRLVDDFLLVTPHLTHA
KTFLRTLVRGVPEYGCVVNLRKTVVNFPVEDEALGGTAFVQMPA
HGLFPWCGLLLDTRTLEVQSDYSSYARTSIRASLTFNRGFKAGR
NMRRKLFGVLRLKCHSLFLDLQVNSLQTVCTNIYKILLLQAYRF
HACVLQLPFHQQVWKNPTFFLRVISDTASLCYSILKAKNAGMSL
GAKGAAGPLPSEAVQWLCHQAFLLKLTRHRVTYVPLLGSLRTAQ
TQLSRKLPGTTLTALEAAANPALPSDFKTILD
```

Figure 2

```
   1 gcagcgctgc gtcctgctgc gcacgtggga agccctggcc ccggccaccc ccgcgatgcc
  61 gcgcgctccc cgctgccgag ccgtgcgctc cctgctgcgc agccactacc gcgaggtgct
 121 gccgctggcc acgttcgtgc ggcgcctggg gccccagggc tggcggctgg tgcagcgcgg
 181 ggacccggcg gctttccgcg cgctggtggc ccagtgcctg gtgtgcgtgc cctgggacgc
 241 acggccgccc cccgccgccc cctccttccg ccaggtgtcc tgcctgaagg agctggtggc
 301 ccgagtgctg cagaggctgt gcgagcgcgg cgcgaagaac gtgctggcct tcggcttcgc
 361 gctgctggac ggggccgcg gggccccca cgaggccttc accaccagcg tgcgcagcta
 421 cctgcccaac acggtgaccg acgcactgcg ggggagcggg gcgtgggggc tgctgctgcg
 481 ccgcgtgggc gacgacgtgc tggttcacct gctggcacgc tgcgcgctct ttgtgctggt
 541 ggctcccagc tgcgcctacc aggtgtgcgg gccgccgctg taccagctcg gcgctgccac
 601 tcaggcccgg cccccgccac acgctagtgg accccgaagg cgtctgggat gcgaacgggc
 661 ctggaaccat agcgtcaggg aggccggggt cccctgggc ctgccagccc cgggtgcgag
 721 gaggcgcggg ggcagtgcca gccgaagtct gccgttgccc aagaggccca ggcgtggcgc
 781 tgccccctgag ccggagcgga cgcccgttgg gcaggggtcc tgggcccacc cgggcaggac
 841 gcgtggaccg agtgaccgtg gtttctgtgt ggtgtcacct gccagacccg ccgaagaagc
 901 cacctctttg gagggtgcgc tctctggcac gcgccactcc cacccatccg tgggccgcca
 961 gcaccacgcg ggccccccat ccacatcgcg gccaccacgt ccctgggaca cgccttgtcc
1021 cccggtgtac gccgagacca agcacttcct ctactcctca ggcgacaagg agcagctgcg
1081 gccctccttc ctactcagct ctctgaggcc cagcctgact ggcgctcgga ggctcgtgga
1141 gaccatcttt ctgggttcca ggccctggat gccagggact ccccgcaggt tgccccgcct
1201 gccccagcgc tactggcaaa tgcggcccct gtttctggag ctgcttggga accacgcgca
1261 gtgcccctac ggggtgctcc tcaagacgca ctgcccgctg cgagctgcgg tcaccccagc
1321 agccggtgtc tgtgcccggg agaagcccca gggctctgtg gcggccccccg aggaggagga
1381 cacagacccc cgtcgcctgg tgcagctgct ccgccagcac agcagccct ggcaggtgta
1441 cggcttcgtg cgggcctgcc tgcgccggct ggtgccccca ggcctctggg gctccaggca
1501 caacgaacgc cgcttcctca ggaacaccaa gaagttcatc tccctgggga agcatgccaa
1561 gctctcgctg caggagctga cgtggaagat gagcgtgcgg gactgcgctt ggctgcgcag
1621 gagcccaggg gttggctgtg ttccggccgc agagcaccgt ctgcgtgagg agatcctggc
1681 caagttcctg cactggctga tgagtgtgta cgtcgtcgag ctgctcaggt ctttcttta
1741 tgtcacggag accacgtttc aaaagaacag gctcttttc taccggaaga gtgtctggag
1801 caagttgcaa agcattggaa tcagacagca cttgaagagg gtgcagctgc gggagctgtc
1861 ggaagcagag gtcaggcagc atcgggaagc caggcccgcc ctgctgacgt ccagactccg
1921 cttcatcccc aagcctgacg ggctgcggcc gattgtgaac atggactacg tcgtgggagc
1981 cagaacgttc cgcagagaaa agagggccga gcgtctcacc tcgagggtga aggcactgtt
2041 cagcgtgctc aactacgagc gggcgcgcg cccggccctc ctgggcgcct ctgtgctggg
2101 cctggacgat atccacaggg cctggcgcac cttcgtgctg cgtgtgcggg cccaggaccc
2161 gccgcctgag ctgtactttg tcaaggtgga tgtgacgggc gcgtacgaca ccatccccca
2221 ggacaggctc acggaggtca tcgccagcat catcaaaccc cagaacacgt actgcgtgcg
2281 tcggtatgcc gtggtccaga aggccgccca tgggcacgtc cgcaaggcct tcaagagcca
2341 cgtctctacc ttgacagacc tccagccgta catgcgacag ttcgtggctc acctgcagga
2401 gaccagcccg ctgagggatg ccgtcgtcat cgagcagagc tcctccctga atgaggccag
2461 cagtgccctc ttcgacgtct tcctacgctt catgtgccac cacgccgtgc gcatcagggg
2521 caagtcctac gtccagtgcc aggggatccc gcagggctcc atcctctcca cgctgctctg
2581 cagcctgtgc tacggcgaca tggagaacaa gctgtttgcg gggattcggc gggacgggct
2641 gctcctgcgt ttggtggatg atttcttgtt ggtgacacct cacctcaccc acgcgaaaac
2701 cttcctcagg accctggtcc gagctgtccc tgagtatggc tgcgtggtga acttgcggaa
2761 gacagtggtg aacttcccctg tagaagacga ggccctgggt ggcacggctt ttgttcagat
2821 gccggccac ggcctattcc cctggtgcgg cctgctgctg gatacccgga ccctggaggt
2881 gcagagcgac tactccagct atgcccggac ctccatcaga gccagtctca ccttcaaccg
2941 cggcttcaag gctgggagga acatgcgtcg caaactcttt ggggtcttgc ggctgaagtg
3001 tcacagcctg tttctggatt tgcaggtgaa cagcctccag acggtgtgca ccaacatcta
3061 caagatcctc ctgctgcagg cgtacaggtt tcacgcatgt gtgctgcagc tcccatttca
3121 tcagcaagtt tggaagaacc ccacattttt cctgcgcgtc atctctgaca cggcctccct
3181 ctgctactcc atcctgaaag ccaagaacgc agggatgtcg ctgggggcca agggcgccgc
3241 cggccctctg ccctccgagg ccgtgcagtg gctgtgccac caagcattcc tgctcaagct
3301 gactcgacac cgtgtcacct acgtgccact cctggggtca ctcaggacag cccagacgca
3361 gctgagtcgg aagctcccgg ggacgacgct gactgccctg gaggccgcag ccaacccggc
3421 actgcccctca gacttcaaga catcctgca ctgatggcca cccgcccaca gccaggccga
3481 gagcagacac cagcagccct gtcacgccgg gctctacgtc ccaggagagg agggcggcc
3541 cacacccagg cccgcaccgc tgggagtctg aggcctgagt gagtgtttgg ccgaggcctg
3601 catgtccggc tgaaggctga gtgtccggct gaggcctgag cgagtgtcca gccaagggct
3661 gagtgtccag cacacctgcc gtcttcactt ccccacaggc tggcgctcgg ctccacccca
3721 gggccagctt ttcctcacca ggagcccggc ttccactccc cacataggaa tagtccatcc
3781 ccagattcgc cattgttcac ccctcgccct gccctccttt gccttccacc cccaccatcc
3841 aggtggagac cctgagaagg accctgggag ctctgggaat tggagtgac caaaggtgtg
3901 ccctgtacac aggcgaggac cctgcacctg gatgggggtc cctgtgggtc aaattggggg
3961 gaggtgctgt gggagtaaaa tactgaatat atgagttttt cagttttgaa aaaaa
```

DENDRITIC CELL VACCINE CONTAINING TELOMERASE REVERSE TRANSCRIPTASE FOR THE TREAMENT OF CANCER

CROSS-REFERENCE TO RELATED APPLICATIONS

This application is a continuation of International Patent Application PCT/US99/06898, filed Mar. 30, 1999 and designating the U.S., pending; which claims the priority basis of U.S. provisional application 60/112,006, filed Mar. 31, 1998, expired. The PCT application is hereby incorporated herein by reference in its entirety.

Also incorporated herein by reference in their entirety are the following: U.S. applications Ser. No. 08/974,549, U.S. Pat. No. 6,166,178; Ser. No. 08/974,584; Ser. No. 08/915,503, abandoned; Ser. No. 08/912,951; Ser. No. 08/911,312, abandoned; and International Applications PCT/US97/17618 and PCT/US97/17885.

FIELD OF THE INVENTION

The present invention is related to the catalytic protein subunit of human telomerase. The invention provides methods and compositions relating to medicine, immunology, and molecular biology.

BACKGROUND OF THE INVENTION

The following discussion is intended to introduce the field of the present invention to the reader. The citation of references in this section should not be construed as an admission of prior invention.

The telomerase ribonucleoprotein complex is a specialized polymerase that maintains telomeres, the specialized structures at the ends of eukaryotic chromosomes. The length and integrity of telomeres in a cell is correlated with the entry of the cell into a senescent stage (i.e., loss of proliferative capacity), or, alternatively, the ability of a cell to escape senescence. Of particular interest is the correlation observed between telomerase activity in human and other mammalian cells and the development of a neoplastic phenotype. For example, telomerase activity is detected in immortal cell lines and a diverse set of tumor tissues, but is not detected (i.e., was absent or below the assay threshold) in normal somatic cell cultures or normal tissues adjacent to a tumor (see, U.S. Pat. Nos. 5,629,154; 5,489,508; 5,648,215; and 5,639,613; also see, Morin, 1989, *Cell* 59: 521; Shay and Bacchetti, 1997, *Eur. J. Cancer* 33:787; Kim et al., 1994, *Science* 266:201 1; Counter et al., 1992, *EMBO J.* 11:1921; Counter et al., 1994, *Proc. Natl. Acad Sci. U.S.A.* 91, 2900; Counter et al., 1994, *J. Virol.* 68:3410). Moreover, a correlation between the level of telomerase activity in a tumor and the likely clinical outcome of the patient has been reported (e.g., U.S. Pat. No. 5,639,613; Langford et al., 1997, *Hum. Pathol.* 28:416).

Thus, telomerase plays an important role in the control of cell proliferation and in tumorigenesis. For these and other reasons, human telomerase is an ideal target for preventing and treating human diseases relating to cellular proliferation and senescence, such as cancer. The present invention provides immunological methods for preventing and treating these and other diseases in humans and nonhuman animals.

BRIEF SUMMARY OF THE INVENTION

In one aspect, the present invention provides a method of activating a T lymphocyte by contacting the T lymphocyte with a dendritic cell that expresses a telomerase reverse transcriptase (TRT) polypeptide encoded by a recombinant nucleic acid. In various embodiments of the invention, the TRT polypeptide is a human TRT (hTRT) polypeptide, and may have the sequence set forth in FIG. 1, or may have a subsequence thereof. In one embodiment, the hTRT polypeptide is full-length. In one embodiment, the dendritic cell is a human cell. The dendritic cell may contact the T lymphocyte in vivo or in vitro.

In a related aspect, the invention provides a recombinant dendritic cell which comprises a recombinant TRT expression cassette. In one embodiment, the recombinant expression cassette is transduced into a stem cell, and the stem cell is then differentiated into the dendritic cell. In one embodiment, the stem cell is differentiated in vitro. The invention also provides a pharmaceutical composition comprising the aforementioned dendritic cell and a pharmaceutically acceptable carrier.

In another aspect, the invention provides a method of eliciting an immune response in a human patient by (a) obtaining human dendritic cells, (b) transducing a TRT expression cassette into the cells so that they are capable of expressing a hTRT polypeptide, and (c) administering the cells to the human patient. In certain embodiments, the dendritic cells are isolated from the human patient to which they are administered, and/or are obtained from hematopoietic precursor cells.

In yet another aspect, the invention provides a method of eliciting an immune response in a human patient by (a) obtaining human dendritic cells, (b) pulsing the cells with a hTRT antigen, and (c) administering the cells pulsed with the hTRT antigen to the human patient. In certain embodiments, the dendritic cells are isolated from the human patient to which they are administered, and/or are obtained from hematopoietic precursor cells. In one embodiment the cells are pulsed with one or more hTRT antigenic peptides that are less than 50 amino acid residues in length 122

In another aspect, the invention provides a method for identifying a cell expressing hTRT. According to the method, a dendritic cell is transduced with a recombinant expression cassette comprising a nucleic acid encoding a hTRT polypeptide; a T lymphocyte is contacted with the transduced dendritic cell, thereby providing an activated T lymphocyte; and a target cell is contacted with the activated T lymphocyte. The effect of the activated T lymphocyte on the target cell is then monitored.

DESCRIPTION OF THE FIGURES

FIG. 1 shows the amino acid sequence (in the one-letter code) (SEQ. ID NO:2) of a 1132-residue hTRT protein.

FIG. 2 shows a nucleic acid sequence (SEQ. ID NO:1) of a cDNA encoding the hTRT protein shown in FIG. 1.

DETAILED DESCRIPTION OF THE INVENTION

I. Definitions

As used herein, "telomerase reverse transcriptase" (TRT) refers to the catalytic protein subunit of the telomerase ribonucleoprotein particle. TRT from humans has been characterized, human TRT (hTRT) genomic and cDNA sequences have been cloned and their sequences determined. See, e.g., Nakamura et al., 1997, *Science* 277:955 and U.S. patent applications Ser. Nos 08/912,951 and 081974,549, U.S. Pat. No. 6,166,178. The sequence of a full-length native hTRT has been deposited in GenBank (Accession No. AF015950), and plasmid and phage vectors having hTRT coding sequences have been deposited with the American Type Culture Collection, Rockville, Md. (accession numbers 209024, 209016, and 98505). Nonhuman TRT polypeptides (i.e., hTRT homologs) are described in U.S. patent applications Ser. Nos. 08/974,584, 08/974,549, 08/915,503, 08/912, 951. hTRT polypeptides that may be used in the present invention include, in addition to the hTRT polypeptides having amino acid sequences described in the aforecited references and deposits, other naturally occurring variants, including allelic variants and processing variants. As described in detail in patent applications (e.g., U.S. Ser. Nos. 08/912,951 and 08/974,549), it is well within the ability of one of skill to obtain naturally occurring hTRT variants or derivatives, and non-human homologs using the above-mentioned sequences and reagents and using, e.g., standard molecular biological techniques. In certain embodiments of the invention, a hTRT polypeptide or variant (or gene or cDNA encoding such a variant) characteristic of a particular subject (e.g., expressed in tumor cells from the subject) or characteristic of a particular tumor type is used. Such tumor or subject-specific hTRT can be obtained using standard methods, e.g., cloning using hTRT PCR primers, purification using anti-hTRT antibodies, and other techniques. Exemplary uses of hTRT polypeptides and polynucleotides, and nonhuman homologs, are described in additional detail in U.S. patent application Ser. No. 08/974,549 (filed Nov. 19, 1997), 08/974,584 (filed Nov. 19, 1997), 08/915,503 (filed Aug. 14, 1997), 08/912,951 (filed Aug. 14, 1997), 08/911,312 (filed Aug. 14, 1997), 08/854,050 (filed May 9, 1997) U.S. Pat. No. 6,261,836, Ser. No. 08/851,843, (filed May 6, 1997), U.S. Pat. No. 6,093,809, Ser. No. 08/846,017 (filed Apr. 25, 1997) abandoned, 08/844,419 (filed Apr. 18, 1996), abandoned 08/724,643 (filed Oct. 1, 1996) abandoned, and Ser. No. 08/979,742 (filed Nov. 26, 1997), abandoned Each of the aforementioned patent applications is explicitly incorporated herein by reference in its entirety and for all purposes.

A "dendritic cell" (DC) is an antigen presenting cell (APC) with a characteristic morphology including lamellipodia extending from the dendritic cell body in several directions. Several phenotypic criteria are also typical, including high levels of MHC molecules and costimulatory molecules, a lack of markers specific for granulocytes, NK cells, B lymphocytes, and T lymphocytes, but can vary depending on the source of the dendritic cell. DCs are able to initiate antigen specific primary T lymphocyte responses in vitro and in vivo, and direct a strong mixed leukocyte reaction (MLR) compared to peripheral blood leukocytes, splenocytes, B cells and monocytes. DCs can be derived from a hematopoietic stem cell, e.g., a CD34$^+$ precursor cell. Dendritic cells are described generally by Steinman, 1991, *Annu Rev Immunol.* 9:271–96.

A cell is "transduced" with a selected nucleic acid when the nucleic acid is translocated into the cell. A cell is "stably transduced" with a selected nucleic acid when the selected nucleic acid is replicated and passed on to progeny cells. A cell is "transformed" with a selected nucleic acid when the selected nucleic acid is integrated into the cell's genome.

A "TRT expression cassette" is a nucleic acid construct, generated recombinantly or synthetically, that includes a nucleic acid encoding a TRT polypeptide or fragment, and a promoter. In some embodiments, the expression cassette also includes other genetic elements, e.g., an origin of replication, and/or chromosome integration elements such as retroviral LTRs. The TRT expression cassette may be plasmid, virus genome, nucleic acid fragment, or the like.

The term "recombinant" has its usual meaning in the art. Thus, a recombinant polynucleotide is a polynucleotide synthesized or otherwise manipulated in vitro (e.g., using molecular biological techniques), and is typically linked to sequence (e.g., a heterologous promoter, vector sequence or other sequence) with which it is not normally linked in nature and/or comprises mutations (e.g., deletions) compared to naturally occurring forms; a "recombinant polypeptide" is a polypeptide that is produced by expression of a recombinant nucleotide; and a "recombinant cell" is a cell comprising a recombinant polynucleotide.

The terms "activation" or "activating," when used in reference to a T lymphocyte, has the ordinary meaning in the art of immunology and refers to characteristic changes (e.g., calcium ion influx, tyrosine kinase activation) that follow ligand-receptor interactions between a T lymphocyte and antigen presenting cell. T cell activation ordinarily results in clonal expansion of antigen-reactive T lymphocytes.

II. Introduction

The methods and reagents of the invention are useful for eliciting an in vivo immune response to telomerase, a telomerase protein, and/or a cell expressing telomerase or a telomerase protein. In particular, the methods and reagents of the invention are used to treat or prevent diseases or conditions related to cell proliferation, such as cancers.

In humans and other mammals, many cells that proliferate indefinitely, such as cancer cells, are characterized by the expression of the endogenous telomerase reverse transcriptase (TRT) gene and the presence of detectable telomerase activity. In contrast, most normal somatic cells in mammals have no or very low levels of TRT expression. Thus, by eliciting a specific immune response to TRT or to TRT-expressing cells, it is possible to selectively target proliferating cells for immunological destruction. Reagents, such as the dendritic cells described infra, that induce differentiation and proliferation of T lymphocytes that specifically target telomerase expressing cells may be used for the prevention or treatment of cancer. Induction of an anti-TRT immune response in a human or nonhuman subject will inhibit growth of a tumor in the subject, and/or result in regression of the tumor. The methods and reagents (e.g., cells) of the invention may also be used prophylactically, to elicit an immune response that decreases a subject's risk of developing a cancer.

According to the present invention, an immune response in a subject may be elicited by administration of TRT proteins and fragments and derivatives thereof, polynucleotides encoding such TRT proteins, fragments, and derivatives, and antigen presenting cells (e.g., dendritic cells) comprising the aforementioned polypeptide and polynucleotide reagents, e.g., dendritic cells displaying TRT antigens in the context of peptide/MHC complexes. The immune response that is evoked may be primarily humoral (i.e., antibody meditated), primarily cell-mediated (e.g., cytotoxic T-lymphocyte-mediated), or have both humoral and cellular components. Alternatively, T lymphocytes may be activated ex vivo and administered to a subject.

Thus, in various aspects of the invention, the immune response to TRT or a TRT-expressing cell is elicited by methods including one or more of the steps of (1) administering to a subject an antigen presenting cell (APC) that presents a TRT antigenic peptide; (2) administering to a subject T-lymphocytes that recognize a TRT peptide/MHC complex; (3) administering an immunogenic amount of a polynucleotide encoding a TRT protein, polypeptide, or fragment; (4) administering an immunogenic amount of a TRT protein, polypeptide, or fragment. The polynucleotide of (3) or polypeptide. of (4) are usually administered in an amount capable of inducing a Class I MHC-restricted cytotoxic T-lymphocyte response against cells expressing a TRT protein or, alternatively, in an amount capable of inducing the production of antibodies by the subject.

II. The Use of Antigen Presenting Cell (APCs) to Elicit an Anti-TRT Immune Response In one embodiment of the invention, antigen presenting cells (APCs) are used to activate T lymphocytes in vivo or ex vivo, to elicit an immune response against TRT-expressing cells. APCs are highly specialized cells, including macrophages, monocytes, and dendritic cells (DCs), that can process antigens and display their peptide fragments on the cell surface together with molecules required for lymphocyte activation Generally, however, dendritic cells are superior to other antigen presenting cells for inducing a T lymphocyte mediated response (e.g., a primary immune response). DCs may be classified into subgroups, including, e.g., follicular dendritic cells, Langerhans dendritic cells, and epidermal dendritic cells.

DCs have been shown to be potent simulators of both T helper (Th) and cytotoxic T lymphocyte (CTL) responses. See Schuler et al., 1997, *Int. Arch. Allergy Immunol.* 112:317–22. In vivo, DCs display antigenic peptides in complexes with MHC class I and MHC class II proteins, The loading of MHC class I molecules usually occurs when cytoplasmic proteins (including proteins such as TRT that are ultimately transported to the nucleus) are processed and transported into the secretory compartments containing the MHC class I molecules. MHC Class II proteins are normally loaded in vivo following sampling (e.g., by endocytosis) by APCsof the extracellular milieu. DCs migrate to lymphoid organs where they induce proliferation and differentiation of antigen-specific T lymphocytes, i.e., Th cells that recognize the peptide/MHC Class II complex and CTLs that recognize the peptide/MHC Class I complex. An introduction to T lymphocytes and cell mediated immunity is found in Paul, 1993, FUNDAMENTAL IMMUNOLOGY, THIRD EDITION Raven Press, New York, N.Y. and the references cited therein.

It is now understood that DCs (or DC precursor cells) can be exposed to antigenic peptide fragments ex vivo (referred to as "antigen pulsing"), or genetically modified ex vivo to express a desired antigen, and subsequently administered to a patient to induce an anti-antigen immune response. Alternatively, the pulsed or genetically modified DCs can be cultured ex vivo with T lymphocytes (e.g., HLA-matched T lymphocytes) to activate those T cells that specific for the selected antigen. Of particular relevance to the present invention, antigen-laden DC may be used to boost host defense against tumors (see, e.g., Hsu, et al., 1996, *Nature Med.* 2:52–58; Young et al., 1996, *J. Exp Med.* 183:7–11; McArthur et al., 1998, *J. Immunother.* 21:41–47; Tuting et al., 1997, *Eur. J. Immunol.* 27:2702–2707; Nair et al., 1997, *Int. J. Cancer* 70:706–715). It will be appreciated that is not necessary that the target antigen (e.g., target "tumor" antigen) be expressed naturally on the cell surface, because cytoplasmic proteins and nuclear proteins, such as TRT, are normally processed, attached to MHC-encoded products intracellularly, and translocated to the cell surface as a peptide/MHC complex.

In one aspect, the present invention relates to the use of polypeptides and polynucleotides encoding TRT (especially human hTRT), and antigen presenting cells (especially dendritic cells), to elicit an immune response against TRT-expressing cells, such as cancer cells, in a subject Typically, this involves (1) isolating a hematopoietic stem cells, (2) genetically modifying the cells to express a TRT polypeptide, (3) differentiating the precursor cells into DCs and (4) administering the DCs to the subject (e.g., human patient). In an alternative embodiment, the process involves (1) isolating DCs (or isolation and differentiation of DC precursor cells) (2) pulsing the cells with TRT peptides, and (3) administering the DCs to the subject These approaches are discussed in greater detail, infra. In a related embodiment, the TRT pulsed or expressing DCs of the invention are used to activate T lymphocytes ex vivo. It will be recognize however, that many variations of each of the procedures described infra are known to those of skill (see, e.g., WO97/29182; WO 97/04802; WO 97/22349; WO 96/23060; WO 98/01538; Hsu et al., 1996, *Nature Med.* 2:52–58), and that still other variations may be discovered in the future.

A. Genetic Modification of Dendritic Cell Precursor

In one embodiment, DC stem cells are isolated for transduction with a TRT-encoding polynucleotide, and induced to differentiate into dendritic cells. The genetically modified DCs express the TRT polypeptide, and display peptide fragments on the cell surface.

(1) Isolation of DC Precursor Cells

Many methods are known for isolating DC precursor cells suitable for transfection with a recombinant TRT-encoding nucleic acid. Human hematopoietic progenitor and stem cells are characterized by the presence of a CD34 surface membrane antigen, which may be used in purification. In one embodiment, for example, human hematopoietic stem cells are obtained by bone marrow aspiration, and the bone marrow mononuclear cells are separated from the other components by means of Ficol density gradient centrifugation and adherence to plastic. The light density, non-adherent cells are obtained and further selected using an anti-CD34 antibody (preferably monoclonal) by standard methods (e.g., incubation of cells with the anti-CD34 antibody, subsequent binding to an immobilized secondary antibody, and removal of nonbound components; see, e.g., Harlow and Lane, 1988, ANTIBODIES: A LABORATORY MANUAL, Cold Spring Harbor Laboratory, New York) Alternatively, cells can be obtained by leukapheresis of peripheral blood and anti-CD34 chromatography (see, e.g., Reeves et al, 1996, *Cancer Res.* 56:5672–77).

(2) Genetic Modification of Cells to Express a TRT Polypeptide

In one embodiment of the invention, the DC or DC precursor cell is genetically modified to express a TRT polypeptide (e.g., transduced ex vivo with a polynucleotide encoding TRT). Exogenous TRT-encoding polynucleotides may be incorporated into DC as TRT expression cassettes using methods such as those described infra. Typically the DC is transformed with an expression cassette comprising a region encoding a TRT polypeptide (or one or more fragments thereof). Upon expression of the TRT expression cassette in the cell, the TRT polypeptide is processed into antigenic peptides expressed on the surface of the DC as complex with MHC class I and II surface molecules. Typically the TRT expression cassette includes an operably linked promoter (to drive expression of the TRT coding sequences). Usually a strong promoter such as a t-RNA pol III promoter, or a pol II promoter with strong constitutive expression is used. Suitable promoters include the constitutive adenovirus major late promoter, the dexamethasone-inducible MMIV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art. In alternative embodiments, the TRT coding sequence is introduced into the DC precursor without a linked promoter. In such a case the TRT transcription is directed by an endogenous promoter (e.g., following integration of the TRT coding sequence into the cell chromosome) or a separately introduced promoter (e.g., that becomes linked by recombination). Often the TRT expression cassette is contained in an expression vector such as a plasmid or viral vector, which may also include other elements, e.g., an origin of replication, chromosome integration elements such as retroviral LTRs, and/or selection (e.g., drug resistance) sequences.

In one embodiment all of most (e.g., at least about 60%, at least about 75% or at least about 90%) of the TRT protein is expressed (i.e., coded for) in the TRT expression cassette. In some cases, however, a shorter fragment may be expressed. Usually TRT coding sequence will encode at least about 8, more often 12, still more often at least 30 or at least 50 contiguous TRT amino acid residues.

In some embodiments, the TRT polypeptide expressed has a sequence of a naturally occurring TRT. It will be recognized, however, that the invention is not limited to naturally occurring sequences. As already noted, fragments of naturally occurring TRT proteins may be used; in addition, the expressed TRT polypeptide may comprise mutations such as deletions, insertions, or amino acid substitutions when compared to a naturally occurring TRT polypeptide, so long as at least one TRT peptide epitope can be processed by the DC and presented on a MHC class I or II surface molecule. It will be appreciated that it may sometimes be desirable to use TRT sequences other than "wild type," in order to, for example, increase antigenicity of the TRT peptide or to increase TRT peptide expression levels. In some embodiments, the introduced TRT sequences encode TRT variants such as polymorphic variants (e.g., a variant expressed by a particular human patient) or variants characteristic of a particular cancer (e.g., a cancer in a particular patient).

The TRT expression sequence may be introduced (transduced) into DCs or stem cells in any of a variety of standard methods, including transfection, recombinant vaccinia viruses, adeno-associated viruses (AAVs), and retroviruses (see, e.g., Reeves et al., 1996, *Cancer Res.* 56:5672; Brossart et al., 1997, *J. Immunol.* 158:3270; Ribas et al., 1997, *Canc. Res.* 57:2865; Carter et al., 1993, WO 93/24641; Kotin, 1994, *Human Gene Therapy* 5:793–801; Specht et al., 1997, *J. Exp. Med.* 186:1213–1221), particle-mediated gene transfer technology (Tuting et al., 1997, *Eur J Immunol.*, 27:2702–2707), or other conventional methods for transforming stem cells are known (e.g., calcium phosphate precipitation; see e.g., Krieger, 1990, *GENE TRANSFER AND EXPRESSION—A LABORATORY MANUAL*, Stockton Press, New York, N.Y.; Sambrook et al., 1989, *MOLECULAR CLONING A LABORATORY MANUAL* 2ND ED, Vol. 1–3; and Ausubel et al., eds, 1997, *CURRENT PROTOCOLS IN MOLECULAR BIOLOGY*, John Wiley & Sons, Inc.). Alternately, TRT-encoding polynucleotide can be packaged into viral particles using packaging cell lines, which are incubated with the DC stem cells.

(3) Differentiation of Precursor Cells into DCs

The TRT-peptide expressing hematopoietic progenitor cells described supra are induced to differentiate into DCs by conventional methods, e.g., by exposure to cytokines such as granulocyte macrophage colony-stimulating factor (GM-CSF), flt-3 ligand, tumor necrosis factor alpha c-kit ligand (also called steel factor or mast cell factor). The addition of interleukin-4 (IL-4) to monocyte cultures is reported to help direct cells to develop as dendritic cells, and TNF-alpha, when mixed with undifferentiated stem cells, increases the likelihood that the stem cells will develop as dendritic cells (see Szaboles et al., 1995, *J. Immunol.* 154:5851–5861). Alternatively, calcium ionophore is used to stimulate the maturation of isolated monocytes into dendritic cells (U.S. Pat. No. 5,643,786). In one embodiment, DCs are obtained from CD34+ hematopoietic progenitor cells from the blood (e.g., of cancer patients) according to the method described by Bernhard et al., 1995, *Cancer Res.* 55:1099–104. A DC maturation factor may be used to cause "immature DCs" to stably express dendritic cell characteristics (e.g., dendritic cell markers p55 and CD83; see WO 97/29182). Alternatively, immature DCs may be used to activate T cells (Koch et al., 1995, *J. Immunol.* 155:93–100).

The culture of cells such as those used in conjunction with the present invention, including stem cells and dendritic cells is well known in the art (see, e.g., Freshney, 1994, *CULTURE OF ANIMAL CELLS, A MANUAL OF BASIC TECHNIQUE, THIRD EDITION* Wiley-Liss, New York).

(4) Administering the DCs to the Subject (e.g. Human Patient

The transformed DCs of the invention are introduced into the subject (e.g., human patient) where they induce a immune response. Typically the immune response includes a CTL response against target cells bearing TRT antigenic peptides (e.g., in a MHC class I/peptide complex). These target cells are typically cancer cells.

When the DCs of the invention are to be administered to a patient, they are preferably isolated from, or derived from precursor cells from, that patient (i.e., the DCs are administered to an autologous patient). However, the cells may be infused into HLA-matched allogeneic, or HLA-mismatched allogenic patients. In the latter case, immunosuppressive drugs may be administered to the recipient.

The cells are administered in any suitable manner, preferably with a pharmaceutically acceptable carrier (e.g., saline). Usually administration will be intravenous, but intra-articular, intramuscular, intradermal, intraperitoneal, and subcutaneous routes are also acceptable. Administration (i.e., immunization) may be repeated at time intervals. Infusions of DC may be combined with administration of cytokines that act to maintain DC number and activity (e.g., GM-CSF, IL-12)

The dose administered to a patient, in the context of the present invention should be sufficient to induce an immune response as detected by assays which measure T cell proliferation, T lymphocyte cytotoxicity, and/or effect a beneficial therapeutic response in the patient over time, e.g., to inhibit growth of cancer cells or result in reduction in the number of cancer cells or the size of a tumor. Typically, $10^6$ to $10^9$ or more DCs are infused, if available.

B. Peptide Pulsing of Dendritic Cells

In a related embodiment of the invention, DCs are obtained (either from a patient or by in vitro differentiation of precursor cells) and pulsed with antigenic peptides having a sequence of TRT (e.g., hTRT). The pulsing results in the presentation of TRT peptides onto the surface MHC molecules of the cells. The TRT-peptide/MHC complexes displayed on the cell surface are capable of inducing a MHC-restricted cytotoxic T-lymphocyte response against target cells expressing TRT polypeptides (e.g., cancer cells).

(1) Isolation of DCs

DCs can be obtained by isolating DC precursor cells and inducing them to differentiate into DCs, as described supra. Alternatively, DCs may be isolated from both lymphoid and non-lymphoid tissues; typically they are purified from peripheral blood. Methods for isolation of human DCs from blood include apheresis followed by procedures involving density gradient methods, positive selection (e.g., affinity chromatography with antibodies directed to DC surface markers), negative selection, or combinations thereof (see, e.g., WO97122349; WO95134638; WO98/01538; WO94/02156).

DC may be isolated from a normal human or from a patient suffering from a disease. In either case, individuals may be treated with colony stimulating factors to increase their number of DC prior to isolation. For example, GM-CSF, may be infused into an individual at 250 $\mu$g/m$^2$/day for several days up to three weeks intravenously prior to obtaining the peripheral blood mononuclear leukocytes (PBML) for the purification of DC. This procedure may increase the yield of DC for antigen pulsing and subsequent It will be appreciated that, in one embodiment of the invention, "immortalized" or "extended life span dendritic cells" are used. Immortalized DCs may be prepared according to the methods of copending applications U.S. Ser. No. 08/912,951 and 08/974,549. In an alternative embodiment, DCs transformed with Epstein-Barr virus (see, WO 97/04802), retroviral vectors containing an oncogene (see, e.g, WO 94/28113) and the like (U.S. Pat. No. 5,648,219) may be used (2) Pulsing DCs with TRT Peptides DCs are exposed ex vivo to TRT antigens, and allowed to process the antigen so that TRT epitopes are presented on the surface of the cell in the context of a MHC class I (or MHC class II) complex. This procedure is referred to as "antigen pulsing." The "pulsed DCs" may then be used to activate T lymphocytes.

The TRT peptide antigens used for pulsing DCs comprise at least one linear epitopes derived from the TRT protein. TRT proteins or substantial fragments thereof may be used, as they will be taken up and processed by the DCs. Alternatively, short "peptides" may be administered to the DCs.

When TRT peptides are used for pulsing, they will usually have at least about 6 or 8 amino acids and fewer than about 30 amino acids or fewer than about 50 amino acid residues in length In one embodiment, the immunogenic TRT peptide has between about 8 and 12 amino acids. A mixture of hTRT protein fragments may be used; alternatively a particular peptide of defined sequence may be used. The TRT peptide antigens may be produced by de novo peptide synthesis, enzymatic digestion of purified or recombinant hTRT, by purification of telomerase from a natal source (e.g., a patient or tumor cells from a patient), or expression of a recombinant polynucleotide encoding a hTRT fragment.

It has been found that the various class I MHC alleles bind peptides having, from N-terminus to C-terminus, first, second and/or third conserved amino acid residues separated by a certain number of amino acids. The binding motifs for several human HLA-A alleles are provided in WO 94/03205. Thus, in one embodiment of the invention, the TRT fragment or peptide comprises at least one linear TRT epitope having a class I MHC binding motif, and, in particular, an HLA-A1 binding motif, an HLA-A2.1 binding motif, an HLA-A3.2 binding motif an HLA-A11 binding motif, an HLA-A24.1 binding motif or an HLA-B7 binding motif Provided with the nucleic acid and protein sequences of a TRT, such as the hTRT sequences provided in FIG. 1 and FIG. 2, it is within the ability of one of ordinary skill to identify and produce various large or small polypeptides or peptides that comprise particular HLA binding motifs. If desired, a mixture of TRT peptides may be used, so that a wide variety of HLA binding motifs are represented.

The amount of TRT antigen used for pulsing DC will depend on the nature, size and purity of the peptide or polypeptide. Typically, from about 0.05 $\mu$g/ml to about 1 mg/ml, most often from about 1 to about 100 $\mu$g/ml of TRT peptide is used. After adding the TRT peptide antigen(s) to the cultured DC, the cells are then allowed sufficient time to take up and process the antigen and express antigen peptides on the cell surface in association with either class I or class II MHC. Typically this occurs in about 18–30 hours, most often about 24 hours. In one exemplary embodiment enriched DC are resuspended ($10^6$ cells/ml) in RPMI media (Gibco) and cultured with (50 ug/ml) hTRT peptide antigens overnight under standard conditions (e.g., 37° C. humidified incubator/5% CO2).

(3) Administering the DCs to the Subject

The pulsed DC are washed in physiologic saline and administered to a subject as described supra, Section (A)(4).

C) Administration of TRT-Reactive T Lymphocytes

Antigen-specific T lymphocytes may be prepared ex vivo by collecting naive T lymphocytes from an individual (e.g., CD8+ T lymphocytes), contacting them with the DCs of the invention (e.g., TRT transformed or pulsed DCs) so that TRT-reactive T lymphocytes proliferate. In an alternative embodiment, the DCs are pulsed with TRT antigens at the time of co-culture with T lymphocytes. The expanded TRT-reactive T lymphocyte population may then be administered to the individual, or may be used for in vitro assays. When administered to a patient, the ex vivo activated-T lymphocytes are cytotoxic against target cells bearing TRT antigenic peptides, such as cancer cells (see, e.g., WO 94/ 02156).

Several techniques are known for isolating T lymphocytes. In one method, Ficoll-Hypaque density gradient centrifugation is used to separate PBMC from red blood cells and neutrophils according to established procedures. Cells are washed with AIM-V (GIBCO) supplemented with 2 mM glutamine, 10 $\mu$g/ml gentamicin sulfate, 50 $\mu$g/ml streptomycin and 1% fetal bovine serum). Enrichment for T lymphocytes is performed by negative or positive selection with appropriate monoclonal antibodies (e.g., anti-CD2, CD3, CD4, CD5 and CD8) coupled to columns or magnetic beads according to standard techniques. Alternatively, fluorescence-activated cell sorting is used. An aliquot of cells is analyzed for cell surface phenotype including CD4, CD8, CD3 and CD 14. Cells are washed and resuspended at a concentration of $5 \times 10^5$ cells per ml of AIM-V supplemented as above and containing 5% FBS and 100 U/ml recombinant IL-2. The T lymphocytes are then cultured with pulsed or genetically modified DCs, optionally in the presence of low doses of IL-4 and IL-2.

The activated T lymphocytes can then be administered to a subject (e.g., infused) as described for DCs, supra. The expanded T lymphocytes may be administered alone, or in combination with lymphokines such as IL-2 and/or IL-4.

IV. IN VITRO ASSAYS

The present invention provides commercially valuable assays, e.g., for identifying TRT-expressing cells. In the assays of the invention, dendritic cells are transformed with a TRT encoding nucleic acid or pulsed with a TRT peptide. The DC is used to activate isolated T lymphocytes, which are then tested for cytotoxic activity against a class of cells though to TRT. Cytotoxicity (e.g., as indicated in a standard assays such as a "$^{51}$Cr release assay," infra) indicates that the cells express TRT is amounts sufficient to mediate a T lymphocyte recognition of the cell. This provides investigators with an assay for TRT-expressing cells.

To demonstrate that CTL have cytolytic activity against a cell (e.g., a cell expressing TRT, such as a cancer cell) the target antigen-presenting cells and effector CTL cells are mixed in culture and target cell lysis is observed. Any suitable method for measuring cell lysis can be used by one skilled in the art. For example, a radioactivity release assay can be used to measure lysis of the target cells. For example, the target cells are labeled with radioactive reagents such as $^{51}$Cr, which are taken up by live cells. Following labeling, the target cells are washed and mixed with specific CTLs. Supernatants are harvested after a suitable time and counted to determine the percent radioactivity release. Other methods to determine the amount of cell lysis include trypan blue exclusion, in which living cells that exclude the dye are counted and compared to a control sample of non-presenting cells treated in the same manner.

All publications and patent documents cited in this application are incorporated by reference in their entirety for all purposes to the same extent as if each individual publication or patent document were so individually denoted.

What is claimed is:

1. A composition comprising antigen-presenting cells containing a polypeptide that comprises at least 6 consecutive amino acids of telomerase reverse transcriptase (TRT; SEQ. ID NO:2), and a pharmaceutical carrier suitable for human administration; whereupon administration of the composition to a human subject induces an anti-TRT immunological response.

2. The composition of claim 1, wherein the antigen-presenting cells are dendritic cells.

3. The composition of claim 1, wherein the antigen-presenting cells have either been pulsed ex vivo with a polypeptide containing said consecutive amino acids, or modified ex vivo with a polynucleotide encoding said consecutive amino acids.

4. The composition of claim 1, wherein the polypeptide comprises at least 8 consecutive amino acids of SEQ. ID NO:2.

5. The composition of claim 1, further comprising a cytokine.

6. The composition of claim 5, wherein the cytokine is GM-CSF or IL-2.

7. The composition of claim 1, wherein the immunological response comprises both TRT-specific antibody and TRT-specific cytotoxic T cells.

8. A method for preparing the composition of claim 1, comprising isolating mononuclear leukocytes from peripheral blood, optionally fractionating or differentiating the leukocytes, and then either:
   a) pulsing the leukocytes with a polypeptide containing said consecutive amino acids; or
   b) modifying the leukocytes with a polynucleotide encoding said consecutive amino acids.

9. The method of claim 8, wherein the leukocytes are pulsed with a polypeptide containing 8–12 consecutive amino acids of SEQ. ID NO:2.

10. The method of claim 8, wherein the leukocytes are modified with a polynucleotide encoding at last 12 consecutive amino acids of SEQ. ID NO:2.

11. A method for eliciting an anti-TRT immunological response in a subject, comprising administering to the subject the composition of claim 1.

12. The composition of claim 1, wherein the antigen-presenting cells contain a plurally of such polypeptides.

13. A method for preparing cytotoxic T cells specific for telomerase reverse transcriptase (TRT), comprising combining T lymphocytes ex vivo with antigen-presenting cells containing a polypeptide that comprises at least 6 consecutive amino acids of telomerase reverse transcriptase (TRT; SEQ. ID NO:2), so as to cause T lymphocytes specific for TRT to proliferate.

14. The method of claim 13, wherein the antigen-presenting cells are dendritic cells.

15. The method of claim 13, wherein the antigen-presenting cells have been pulsed ex vivo with the polypeptide.

16. The method of claim 13, wherein the antigen-presenting cells have been modified with a polynucleotide ex vivo so as to express the polypeptide.

17. A cytotoxic T cell produced according to the method of claim 13.

18. A method for providing a subject with T cell immunity against target cells bearing TRT antigenic peptides, comprising administering to the subject cytotoxic T cells according to claim 17.

19. An isolated cytotoxic T cell specific for telomerase reverse transcriptase (TRT).

20. The cytotoxic T cell of claim 19, which is a CD8+ Class-I restricted T cell.

21. A pharmaceutical composition comprising a plurality of cytotoxic T cells according to claim 19 in a pharmaceutically acceptable carrier suitable for human administration.

22. A method for providing a subject with T cell immunity against target cells bearing TRT antigenic peptides, comprising administering to the subject cytotoxic T cells according to claim 19.

* * * * *

UNITED STATES PATENT AND TRADEMARK OFFICE
CERTIFICATE OF CORRECTION

PATENT NO. : 6,440,735 B1
DATED : August 27, 2002
INVENTOR(S) : Federico C.A. Gaeta It is certified that error appears in the above-identified patent and that said Letters Patent is hereby corrected as shown below:

<u>Title page,</u>
Item [22], the filing date on this patent is -- Sep. 29, 2000 --.

Signed and Sealed this

Twenty-fifth Day of February, 2003

JAMES E. ROGAN
*Director of the United States Patent and Trademark Office*

SEQUENCE LISTING

```
<160> NUMBER OF SEQ ID NOS: 2

<210> SEQ ID NO 1
<211> LENGTH: 4015
<212> TYPE: DNA
<213> ORGANISM: Homo sapiens
<220> FEATURE:
<221> NAME/KEY: CDS
<222> LOCATION: (56)..(3454)
<223> OTHER INFORMATION: human telomerase reverse transcriptase (hTRT)

<400> SEQUENCE: 1
gcagcgctgc gtcctgctgc gcacgtggga agccctggcc ccggccaccc ccgcg atg      58
                                                              Met
                                                                1 ccg cgc gct ccc cgc tgc cga gcc gtg cgc tcc ctg ctg cgc agc cac      106
Pro Arg Ala Pro Arg Cys Arg Ala Val Arg Ser Leu Leu Arg Ser His
         5                  10                  15 tac cgc gag gtg ctg ccg ctg gcc acg ttc gtg cgg cgc ctg ggg ccc      154
Tyr Arg Glu Val Leu Pro Leu Ala Thr Phe Val Arg Arg Leu Gly Pro
     20                  25                  30 cag ggc tgg cgg ctg gtg cag cgc ggg gac ccg gcg gct ttc cgc gcg      202
Gln Gly Trp Arg Leu Val Gln Arg Gly Asp Pro Ala Ala Phe Arg Ala
 35                  40                  45 ctg gtg gcc cag tgc ctg gtg tgc gtg ccc tgg gac gca cgg ccg ccc      250
Leu Val Ala Gln Cys Leu Val Cys Val Pro Trp Asp Ala Arg Pro Pro
 50                  55                  60                  65 ccc gcc gcc ccc tcc ttc cgc cag gtg tcc tgc ctg aag gag ctg gtg      298
Pro Ala Ala Pro Ser Phe Arg Gln Val Ser Cys Leu Lys Glu Leu Val
                 70                  75                  80 gcc cga gtg ctg cag agg ctg tgc gag cgc ggc gcg aag aac gtg ctg      346
Ala Arg Val Leu Gln Arg Leu Cys Glu Arg Gly Ala Lys Asn Val Leu
             85                  90                  95 gcc ttc ggc ttc gcg ctg ctg gac ggg gcc cgc ggg ggc ccc ccc gag      394
Ala Phe Gly Phe Ala Leu Leu Asp Gly Ala Arg Gly Gly Pro Pro Glu
        100                 105                 110 gcc ttc acc acc agc gtg cgc agc tac ctg ccc aac acg gtg acc gac      442
Ala Phe Thr Thr Ser Val Arg Ser Tyr Leu Pro Asn Thr Val Thr Asp
    115                 120                 125 gca ctg cgg ggg agc ggg gcg tgg ggg ctg ctg ctg cgc cgc gtg ggc      490
Ala Leu Arg Gly Ser Gly Ala Trp Gly Leu Leu Leu Arg Arg Val Gly
130                 135                 140                 145 gac gac gtg ctg gtt cac ctg ctg gca cgc tgc gcg ctc ttt gtg ctg      538
Asp Asp Val Leu Val His Leu Leu Ala Arg Cys Ala Leu Phe Val Leu
                150                 155                 160 gtg gct ccc agc tgc gcc tac cag gtg tgc ggg ccg ccg ctg tac cag      586
Val Ala Pro Ser Cys Ala Tyr Gln Val Cys Gly Pro Pro Leu Tyr Gln
            165                 170                 175 ctc ggc gct gcc act cag gcc cgg ccc ccg cca cac gct agt gga ccc      634
Leu Gly Ala Ala Thr Gln Ala Arg Pro Pro Pro His Ala Ser Gly Pro
        180                 185                 190
```

```
cga agg cgt ctg gga tgc gaa cgg gcc tgg aac cat agc gtc agg gag      682
Arg Arg Arg Leu Gly Cys Glu Arg Ala Trp Asn His Ser Val Arg Glu
    195                 200                 205 gcc ggg gtc ccc ctg ggc ctg cca gcc ccg ggt gcg agg agg cgc ggg      730
Ala Gly Val Pro Leu Gly Leu Pro Ala Pro Gly Ala Arg Arg Arg Gly
210                 215                 220                 225 ggc agt gcc agc cga agt ctg ccg ttg ccc aag agg ccc agg cgt ggc      778
Gly Ser Ala Ser Arg Ser Leu Pro Leu Pro Lys Arg Pro Arg Arg Gly
                230                 235                 240 gct gcc cct gag ccg gag cgg acg ccc gtt ggg cag ggg tcc tgg gcc      826
Ala Ala Pro Glu Pro Glu Arg Thr Pro Val Gly Gln Gly Ser Trp Ala
            245                 250                 255 cac ccg ggc agg acg cgt gga ccg agt gac cgt ggt ttc tgt gtg gtg      874
His Pro Gly Arg Thr Arg Gly Pro Ser Asp Arg Gly Phe Cys Val Val
        260                 265                 270 tca cct gcc aga ccc gcc gaa gaa gcc acc tct ttg gag ggt gcg ctc      922
Ser Pro Ala Arg Pro Ala Glu Glu Ala Thr Ser Leu Glu Gly Ala Leu
    275                 280                 285 tct ggc acg cgc cac tcc cac cca tcc gtg ggc cgc cag cac cac gcg      970
Ser Gly Thr Arg His Ser His Pro Ser Val Gly Arg Gln His His Ala
290                 295                 300                 305 ggc ccc cca tcc aca tcg cgg cca cca cgt ccc tgg gac acg cct tgt     1018
Gly Pro Pro Ser Thr Ser Arg Pro Pro Arg Pro Trp Asp Thr Pro Cys
                310                 315                 320 ccc ccg gtg tac gcc gag acc aag cac ttc ctc tac tcc tca ggc gac     1066
Pro Pro Val Tyr Ala Glu Thr Lys His Phe Leu Tyr Ser Ser Gly Asp
            325                 330                 335 aag gag cag ctg cgg ccc tcc ttc cta ctc agc tct ctg agg ccc agc     1114
Lys Glu Gln Leu Arg Pro Ser Phe Leu Leu Ser Ser Leu Arg Pro Ser
        340                 345                 350 ctg act ggc gct cgg agg ctc gtg gag acc atc ttt ctg ggt tcc agg     1162
Leu Thr Gly Ala Arg Arg Leu Val Glu Thr Ile Phe Leu Gly Ser Arg
    355                 360                 365 ccc tgg atg cca ggg act ccc cgc agg ttg ccc cgc ctg ccc cag cgc     1210
Pro Trp Met Pro Gly Thr Pro Arg Arg Leu Pro Arg Leu Pro Gln Arg
370                 375                 380                 385 tac tgg caa atg cgg ccc ctg ttt ctg gag ctg ctt ggg aac cac gcg     1258
Tyr Trp Gln Met Arg Pro Leu Phe Leu Glu Leu Leu Gly Asn His Ala
                390                 395                 400 cag tgc ccc tac ggg gtg ctc ctc aag acg cac tgc ccg ctg cga gct     1306
Gln Cys Pro Tyr Gly Val Leu Leu Lys Thr His Cys Pro Leu Arg Ala
            405                 410                 415 gcg gtc acc cca gca gcc ggt gtc tgt gcc cgg gag aag ccc cag ggc     1354
Ala Val Thr Pro Ala Ala Gly Val Cys Ala Arg Glu Lys Pro Gln Gly
        420                 425                 430 tct gtg gcg gcc ccc gag gag gag gac aca gac ccc gtc gcc ctg gtg     1402
Ser Val Ala Ala Pro Glu Glu Glu Asp Thr Asp Pro Arg Arg Leu Val
    435                 440                 445 cag ctg ctc cgc cag cac agc agc ccc tgg cag gtg tac ggc ttc gtg     1450
Gln Leu Leu Arg Gln His Ser Ser Pro Trp Gln Val Tyr Gly Phe Val
450                 455                 460                 465 cgg gcc tgc ctg cgc cgg ctg gtg ccc cca ggc ctc tgg ggc tcc agg     1498
Arg Ala Cys Leu Arg Arg Leu Val Pro Pro Gly Leu Trp Gly Ser Arg
                470                 475                 480 cac aac gaa cgc cgc ttc ctc agg aac acc aag aag ttc atc tcc ctg     1546
His Asn Glu Arg Arg Phe Leu Arg Asn Thr Lys Lys Phe Ile Ser Leu
            485                 490                 495 ggg aag cat gcc aag ctc tcg ctg cag gag ctg acg tgg aag atg agc     1594
Gly Lys His Ala Lys Leu Ser Leu Gln Glu Leu Thr Trp Lys Met Ser
```

-continued

```
              500                 505                 510
gtg cgg gac tgc gct tgg ctg cgc agg agc cca ggg gtt ggc tgt gtt       1642
Val Arg Asp Cys Ala Trp Leu Arg Arg Ser Pro Gly Val Gly Cys Val
    515                 520                 525 ccg gcc gca gag cac cgt ctg cgt gag gag atc ctg gcc aag ttc ctg       1690
Pro Ala Ala Glu His Arg Leu Arg Glu Glu Ile Leu Ala Lys Phe Leu
530                 535                 540                 545 cac tgg ctg atg agt gtg tac gtc gtc gag ctg ctc agg tct ttc ttt       1738
His Trp Leu Met Ser Val Tyr Val Val Glu Leu Leu Arg Ser Phe Phe
                550                 555                 560 tat gtc acg gag acc acg ttt caa aag aac agg ctc ttt ttc tac cgg       1786
Tyr Val Thr Glu Thr Thr Phe Gln Lys Asn Arg Leu Phe Phe Tyr Arg
            565                 570                 575 aag agt gtc tgg agc aag ttg caa agc att gga atc aga cag cac ttg       1834
Lys Ser Val Trp Ser Lys Leu Gln Ser Ile Gly Ile Arg Gln His Leu
        580                 585                 590 aag agg gtg cag ctg cgg gag ctg tcg gaa gca gag gtc agg cag cat       1882
Lys Arg Val Gln Leu Arg Glu Leu Ser Glu Ala Glu Val Arg Gln His
    595                 600                 605 cgg gaa gcc agg ccc gcc ctg ctg acg tcc aga ctc cgc ttc atc ccc       1930
Arg Glu Ala Arg Pro Ala Leu Leu Thr Ser Arg Leu Arg Phe Ile Pro
610                 615                 620                 625 aag cct gac ggg ctg cgg ccg att gtg aac atg gac tac gtc gtg gga       1978
Lys Pro Asp Gly Leu Arg Pro Ile Val Asn Met Asp Tyr Val Val Gly
                630                 635                 640 gcc aga acg ttc cgc aga gaa aag agg gcc gag cgt ctc acc tcg agg       2026
Ala Arg Thr Phe Arg Arg Glu Lys Arg Ala Glu Arg Leu Thr Ser Arg
            645                 650                 655 gtg aag gca ctg ttc agc gtg ctc aac tac gag cgg gcg cgg cgc ccc       2074
Val Lys Ala Leu Phe Ser Val Leu Asn Tyr Glu Arg Ala Arg Arg Pro
        660                 665                 670 ggc ctc ctg ggc gcc tct gtg ctg ggc ctg gac gat atc cac agg gcc       2122
Gly Leu Leu Gly Ala Ser Val Leu Gly Leu Asp Asp Ile His Arg Ala
    675                 680                 685 tgg cgc acc ttc gtg ctg cgt gtg cgg gcc cag gac ccg ccg cct gag       2170
Trp Arg Thr Phe Val Leu Arg Val Arg Ala Gln Asp Pro Pro Pro Glu
690                 695                 700                 705 ctg tac ttt gtc aag gtg gat gtg acg ggc gcg tac gac acc atc ccc       2218
Leu Tyr Phe Val Lys Val Asp Val Thr Gly Ala Tyr Asp Thr Ile Pro
                710                 715                 720 cag gac agg ctc acg gag gtc atc gcc agc atc atc aaa ccc cag aac       2266
Gln Asp Arg Leu Thr Glu Val Ile Ala Ser Ile Ile Lys Pro Gln Asn
            725                 730                 735 acg tac tgc gtg cgt cgg tat gcc gtg gtc cag aag gcc gcc cat ggg       2314
Thr Tyr Cys Val Arg Arg Tyr Ala Val Val Gln Lys Ala Ala His Gly
        740                 745                 750 cac gtc cgc aag gcc ttc aag agc cac gtc tct acc ttg aca gac ctc       2362
His Val Arg Lys Ala Phe Lys Ser His Val Ser Thr Leu Thr Asp Leu
    755                 760                 765 cag ccg tac atg cga cag ttc gtg gct cac ctg cag gag acc agc ccg       2410
Gln Pro Tyr Met Arg Gln Phe Val Ala His Leu Gln Glu Thr Ser Pro
770                 775                 780                 785 ctg agg gat gcc gtc gtc atc gag cag agc tcc tcc ctg aat gag gcc       2458
Leu Arg Asp Ala Val Val Ile Glu Gln Ser Ser Ser Leu Asn Glu Ala
                790                 795                 800 agc agt ggc ctc ttc gac gtc ttc cta cgc ttc atg tgc cac cac gcc       2506
Ser Ser Gly Leu Phe Asp Val Phe Leu Arg Phe Met Cys His His Ala
            805                 810                 815 gtg cgc atc agg ggc aag tcc tac gtc cag tgc cag ggg atc ccg cag       2554
```

-continued

| | |
|---|---|
| Val Arg Ile Arg Gly Lys Ser Tyr Val Gln Cys Gln Gly Ile Pro Gln<br>    820                            825                        830 | |
| ggc tcc atc ctc tcc acg ctg ctc tgc agc ctg tgc tac ggc gac atg<br>Gly Ser Ile Leu Ser Thr Leu Leu Cys Ser Leu Cys Tyr Gly Asp Met<br>    835                            840                        845 | 2602 |
| gag aac aag ctg ttt gcg ggg att cgg cgg gac ggg ctg ctc ctg cgt<br>Glu Asn Lys Leu Phe Ala Gly Ile Arg Arg Asp Gly Leu Leu Leu Arg<br>850                       855                        860                        865 | 2650 |
| ttg gtg gat gat ttc ttg ttg gtg aca cct cac ctc acc cac gcg aaa<br>Leu Val Asp Asp Phe Leu Leu Val Thr Pro His Leu Thr His Ala Lys<br>                      870                        875                        880 | 2698 |
| acc ttc ctc agg acc ctg gtc cga ggt gtc cct gag tat ggc tgc gtg<br>Thr Phe Leu Arg Thr Leu Val Arg Gly Val Pro Glu Tyr Gly Cys Val<br>          885                            890                        895 | 2746 |
| gtg aac ttg cgg aag aca gtg gtg aac ttc cct gta gaa gac gag gcc<br>Val Asn Leu Arg Lys Thr Val Val Asn Phe Pro Val Glu Asp Glu Ala<br>900                       905                        910 | 2794 |
| ctg ggt ggc acg gct ttt gtt cag atg ccg gcc cac ggc cta ttc ccc<br>Leu Gly Gly Thr Ala Phe Val Gln Met Pro Ala His Gly Leu Phe Pro<br>    915                            920                        925 | 2842 |
| tgg tgc ggc ctg ctg ctg gat acc cgg acc ctg gag gtg cag agc gac<br>Trp Cys Gly Leu Leu Leu Asp Thr Arg Thr Leu Glu Val Gln Ser Asp<br>930                       935                        940                        945 | 2890 |
| tac tcc agc tat gcc cgg acc tcc atc aga gcc agt ctc acc ttc aac<br>Tyr Ser Ser Tyr Ala Arg Thr Ser Ile Arg Ala Ser Leu Thr Phe Asn<br>                      950                        955                        960 | 2938 |
| cgc ggc ttc aag gct ggg agg aac atg cgt cgc aaa ctc ttt ggg gtc<br>Arg Gly Phe Lys Ala Gly Arg Asn Met Arg Arg Lys Leu Phe Gly Val<br>    965                            970                        975 | 2986 |
| ttg cgg ctg aag tgt cac agc ctg ttt ctg gat ttg cag gtg aac agc<br>Leu Arg Leu Lys Cys His Ser Leu Phe Leu Asp Leu Gln Val Asn Ser<br>980                       985                        990 | 3034 |
| ctc cag acg gtg tgc acc aac atc tac aag atc ctc ctg ctg cag gcg<br>Leu Gln Thr Val Cys Thr Asn Ile Tyr Lys Ile Leu Leu Leu Gln Ala<br>    995                          1000                      1005 | 3082 |
| tac agg ttt cac gca tgt gtg ctg cag ctc cca ttt cat cag caa gtt<br>Tyr Arg Phe His Ala Cys Val Leu Gln Leu Pro Phe His Gln Gln Val<br>1010                      1015                      1020                      1025 | 3130 |
| tgg aag aac ccc aca ttt ttc ctg cgc gtc atc tct gac acg gcc tcc<br>Trp Lys Asn Pro Thr Phe Phe Leu Arg Val Ile Ser Asp Thr Ala Ser<br>                      1030                      1035                      1040 | 3178 |
| ctc tgc tac tcc atc ctg aaa gcc aag aac gca ggg atg tcg ctg ggg<br>Leu Cys Tyr Ser Ile Leu Lys Ala Lys Asn Ala Gly Met Ser Leu Gly<br>            1045                      1050                      1055 | 3226 |
| gcc aag ggc gcc gcc ggc cct ctg ccc tcc gag gcc gtg cag tgg ctg<br>Ala Lys Gly Ala Ala Gly Pro Leu Pro Ser Glu Ala Val Gln Trp Leu<br>    1060                      1065                      1070 | 3274 |
| tgc cac caa gca ttc ctg ctc aag ctg act cga cac cgt gtc acc tac<br>Cys His Gln Ala Phe Leu Leu Lys Leu Thr Arg His Arg Val Thr Tyr<br>1075                      1080                      1085 | 3322 |
| gtg cca ctc ctg ggg tca ctc agg aca gcc cag acg cag ctg agt cgg<br>Val Pro Leu Leu Gly Ser Leu Arg Thr Ala Gln Thr Gln Leu Ser Arg<br>1090                      1095                      1100                      1105 | 3370 |
| aag ctc ccg ggg acg acg ctg act gcc ctg gag gcc gca gcc aac ccg<br>Lys Leu Pro Gly Thr Thr Leu Thr Ala Leu Glu Ala Ala Ala Asn Pro<br>            1110                      1115                      1120 | 3418 |
| gca ctg ccc tca gac ttc aag acc atc ctg gac tgatggccac cgcccacag<br>Ala Leu Pro Ser Asp Phe Lys Thr Ile Leu Asp<br>    1125                      1130 | 3471 |

```
ccaggccgag agcagacacc agcagccctg tcacgccggg ctctacgtcc cagggaggga    3531
ggggcggccc acacccaggc ccgcaccgct gggagtctga ggcctgagtg agtgtttggc    3591
cgaggcctgc atgtccggct gaaggctgag tgtccggctg aggcctgagc gagtgtccag    3651
ccaagggctg agtgtccagc acacctgccg tcttcacttc cccacaggct ggcgctcggc    3711
tccaccccag ggccagcttt tcctcaccag gagcccggct tccactcccc acataggaat    3771
agtccatccc cagattcgcc attgttcacc cctcgccctg ccctcctttg ccttccaccc    3831
ccaccatcca ggtggagacc ctgagaagga ccctgggagc tctgggaatt tggagtgacc    3891
aaaggtgtgc cctgtacaca ggcgaggacc ctgcacctgg atggggtcc ctgtgggtca     3951 aattgggggg aggtgctgtg ggagtaaaat actgaatata tgagtttttc agttttgaaa    4011
aaaa                                                                 4015

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
  1               5                  10                  15

His Tyr Arg Glu Val Leu Pro Leu Ala Thr Phe Val Arg Arg Leu Gly
                 20                  25                  30

Pro Gln Gly Trp Arg Leu Val Gln Arg Gly Asp Pro Ala Ala Phe Arg
             35                  40                  45

Ala Leu Val Ala Gln Cys Leu Val Cys Val Pro Trp Asp Ala Arg Pro
         50                  55                  60

Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
                100                 105                 110

Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Leu Arg Arg Val
        130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270
```

```
Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
        290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
        370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
                420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
        450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
        530                 535                 540

Leu His Trp Leu Met Ser Val Tyr Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
        610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
        675                 680                 685
```

-continued

```
Ala Trp Arg Thr Phe Val Leu Arg Val Arg Ala Gln Asp Pro Pro
690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
                755                 760                 765

Leu Gln Pro Tyr Met Arg Gln Phe Val Ala His Leu Gln Glu Thr Ser
770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
                820                 825                 830

Gln Gly Ser Ile Leu Ser Thr Leu Leu Cys Ser Leu Cys Tyr Gly Asp
                835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
                900                 905                 910

Ala Leu Gly Gly Thr Ala Phe Val Gln Met Pro Ala His Gly Leu Phe
                915                 920                 925

Pro Trp Cys Gly Leu Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
                980                 985                 990

Ser Leu Gln Thr Val Cys Thr Asn Ile Tyr Lys Ile Leu Leu Leu Gln
                995                 1000                1005

Ala Tyr Arg Phe His Ala Cys Val Leu Gln Leu Pro Phe His Gln Gln
                1010                1015                1020

Val Trp Lys Asn Pro Thr Phe Phe Leu Arg Val Ile Ser Asp Thr Ala
1025                1030                1035                1040

Ser Leu Cys Tyr Ser Ile Leu Lys Ala Lys Asn Ala Gly Met Ser Leu
                1045                1050                1055

Gly Ala Lys Gly Ala Ala Gly Pro Leu Pro Ser Glu Ala Val Gln Trp
                1060                1065                1070

Leu Cys His Gln Ala Phe Leu Leu Lys Leu Thr Arg His Arg Val Thr
                1075                1080                1085

Tyr Val Pro Leu Leu Gly Ser Leu Arg Thr Ala Gln Thr Gln Leu Ser
                1090                1095                1100
```

-continued

```
Arg Lys Leu Pro Gly Thr Thr Leu Thr Ala Leu Glu Ala Ala Ala Asn
1105                1110                1115                1120

Pro Ala Leu Pro Ser Asp Phe Lys Thr Ile Leu Asp
                1125                1130
```